United States Patent [19]

Gruber et al.

[11] 4,172,951

[45] Oct. 30, 1979

[54] (METH)ACRYLIC ACID ESTERS OF TRICYCLO[5.2.1.0.$^{2.6}$]-DECANE DERIVATIVES

[75] Inventors: Werner Gruber, Düsseldorf-Gerresheim; Joachim Galinke, Langenfeld, both of Fed. Rep. of Germany

[73] Assignee: Henkel Kommanditgesellschaft auf Aktien, Düsseldorf-Holthausen, Fed. Rep. of Germany

[21] Appl. No.: 890,014

[22] Filed: Mar. 24, 1978

[30] Foreign Application Priority Data

Apr. 1, 1977 [DE] Fed. Rep. of Germany ....... 2714538

[51] Int. Cl.$^2$ .................... C07C 00/54; C07C 00/60; C07C 00/74; C07C 00/80
[52] U.S. Cl. .................................... 560/84; 526/282; 560/127; 560/194
[58] Field of Search ........................... 560/194, 84, 127

[56] References Cited

U.S. PATENT DOCUMENTS

| | | | |
|---|---|---|---|
| 2,817,673 | 12/1957 | Roelen et al. | 560/194 |
| 3,485,732 | 12/1969 | D'Alelio | 560/199 |
| 3,485,733 | 12/1969 | D'Alelio | 560/199 |

FOREIGN PATENT DOCUMENTS 642263 6/1962 Canada ................................... 560/194

OTHER PUBLICATIONS

Koelbel et al., as cited in Chem. Abstracts, 74, p. 4219d, (1971).

Primary Examiner—Jane S. Myers
Attorney, Agent, or Firm—Hammond & Littell

[57] ABSTRACT

(Meth)acrylic acid esters of tricyclo [5.2.1.0.$^{2.6}$]-decane derivatives having the formula

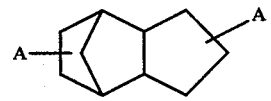

wherein A represents the radical

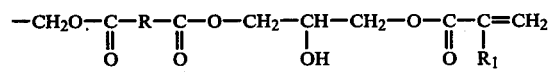

wherein R is a divalent hydrocarbon having 2 to 6 carbon atoms selected from the group consisting of alkylene, alkenylene, cyclohexylene, phenylene and tetrahydrophenylene, and $R_1$ is a member selected from the group consisting of hydrogen and methyl; as well as the process for the production of the esters, and their use in adhesive or sealing compositions which harden under exclusion of oxygen.

5 Claims, No Drawings

(METH)ACRYLIC ACID ESTERS OF TRICYCLO[5.2.1.0.$^{2,6}$]-DECANE DERIVATIVES

BACKGROUND OF THE INVENTION

A method is known for producing acrylic acid esters, optionally substituted on the α carbon atom, of tricyclic decanes which are substituted by hydroxymethyl groups and which are suitable for use as adhesives. In this method, di-(hydroxymethyl)-tricyclo[5.2.1.0.$^{2,6}$]-decanes with hydroxymethyl groups in the 3,8- or 3,9- or 4,8-position, or mixtures thereof are reacted, with acrylic acid, methacrylic acid, acid halides thereof or their esters with lower alkanols, or the esters of the said di-(hydroxymethyl)-decanes with slightly volatile acids are interchanged by ester exchange either with acrylic acid, methacrylic acid or the said esters thereof with lower alkanols.

OBJECTS OF THE INVENTION

An object of the present invention is the development of acid ester derivatives of di-(hydroxymethyl)-tricyclodecane, their reaction products with glycidyl (meth)acrylate and the use of the products of reaction with glycidyl (meth)acrylate as adhesives or sealing agents.

Another object of the present invention is the obtaining of (meth)acrylic acid esters of tricyclo [5.2.1.0.$^{2,6}$]-decane derivatives having the formula

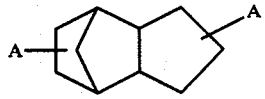

wherein A represents the radical

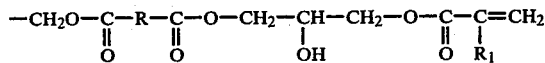

wherein R is a divalent hydrocarbon having 2 to 6 carbon atoms selected from the group consisting of alkylene, alkenylene, cyclohexylene, phenylene and tetrahydrophenylene, and R$_1$ is a member selected from the group consisting of hydrogen and methyl.

A further object of the present invention is the obtaining of tricyclo[5.2.1.0.$^{2,6}$]-decane derivatives having the formula

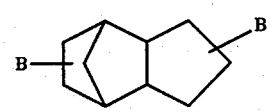

wherein B represents the radical

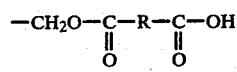

wherein R is a divalent hydrocarbon having 2 to 6 carbon atoms, selected from the group consisting of alkylene, alkenylene, cyclohexylene, phenylene and tetrahydrophenylene.

A yet further object of the present invention is the development of a method for the production of said (meth)acrylic acid ester of tricyclo[5.2.1.0.$^{2,6}$]-decane derivative consisting essentially of reacting one mol of di-(hydroxymethyl)-tricyclo[5.2.1.0.$^{2,6}$]-decane, having hydroxymethyl groups in the 3,8-position or the 3,9-position or the 4,8-position or mixtures thereof, with 2 mols of an acid anhydride having the formula

wherein R is a divalent hydrocarbon having 2 to 6 carbon atoms selected from the group consisting of alkylene, alkenylene, cyclohexylene, phenylene and tetrahydrophenylene, reacting 1 mol of the tricyclo[5.2.1.0.$^{2,6}$]-decane derivatives obtained, having the formula

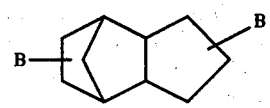

wherein B represents the radical

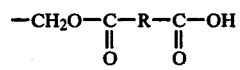

wherein R has the above-assigned values, with 2 mols of glycidyl (meth)acrylate, having the formula

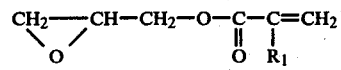

wherein R$_1$ is a member selected from the group consisting of hydrogen and methyl, and recovering said (meth)acrylic acid ester of tricyclo[5.2.1.0.$^{2,6}$]-decane derivatives.

A still further object of the present invention is the development of an anaerobically setting adhesive and sealing composition comprising methacrylic or acrylic acid esters and organic hydroperoxides, which contains from 10% to 90% by weight based on the total weight of the polymerizable portion of the composition of the above (meth)acrylic acid esters of tricyclo[5.2.1.0.$^{2,6}$]-decane derivatives.

These and other objects of the present invention will become more apparent as the description thereof proceeds.

DESCRIPTION OF THE INVENTION

We have now found that novel, valuable compounds, particularly compounds producing satisfactory adhesives, can be obtained when di-(hydroxymethyl)-tricyclo[5.2.1.0.$^{2,6}$]-decanes, with hydroxymethyl groups in the 3,8-position or the 3,9-position or the 4,8-position, or mixtures thereof, are reacted with dicarboxylic acid anhydrides in the molar ratio 1:2, and the acid esters obtained are reacted with glycidyl (meth)acrylate in the molar ratio 1:2.

The compounds of the invention therefore are (meth)acrylic acid esters of tricyclo[5.2.1.0.$^{2,6}$]-decane derivatives having the formula

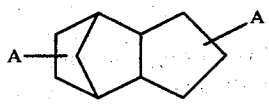

wherein A represents the radical

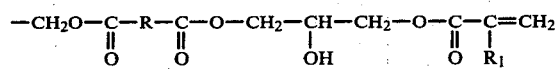

wherein R is a divalent hydrocarbon having 2 to 6 carbon atoms selected from the group consisting of alkylene, alkenylene, cyclohexylene, phenylene and tetrahydrophenylene, and $R_1$ is a member selected from the group consisting of hydrogen and methyl. These compounds are produced by the process consisting essentially of reacting one mol of di-(hydroxymethyl)-tricyclo[5.2.1.0.$^{2.6}$]-decane, having hydroxymethyl groups in the 3,8-position or the 3,9-position or the 4,8-position or mixtures thereof, with 2 mols of an acid anhydride having the formula

wherein R is a divalent hydrocarbon having 2 to 6 carbon atoms selected from the group consisting of alkylene, alkenylene, cyclohexylene, phenylene and tetrahydrophenylene, reacting 1 mol of the tricyclo[5.2.1.0.$^{2.6}$]-decane derivatives obtained, having the formula

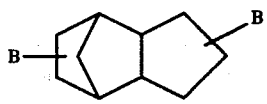

wherein B represents the radical

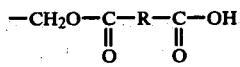

wherein R has the above-assigned values, with 2 mols of glycidyl (meth)acrylate, having the formula

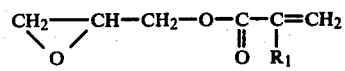

wherein $R_1$ is a member selected from the group consisting of hydrogen and methyl, and recovering said (meth)acrylic acid ester of tricyclo[5.2.1.0.$^{2.6}$]-decane derivatives.

Advantageously, the starting material used for producing the compounds in accordance with the invention are di-(hydroxymethyl)-decanes such as are readily obtained in a known manner by the oxo synthesis by reacting carbon monoxide and hydrogen with dicyclopentadiene in the presence of catalysts such as cobalt compounds, and subsequent hydrogenation of the tricyclo-decane dialdehyde formed. For practical reasons, it is advantageous to use the mixture of the isomeric di-(hydroxymethyl)-tricyclo-decanes produced. However, if it is desired to produce individual compounds, the isomeric diols can be separated and reaction of the invention is subsequently effected on the individual di-(hydroxymethyl)-tricyclo-decanes.

The process of the invention consists essentially of reacting one mol of di-(hydroxymethyl)-tricyclo[5.2.1.0.$^{2.6}$]-decane, having hydroxymethyl groups in the 3,8-position or the 3,9-position or the 4,8-position or mixtures thereof, with 2 mols of an acid anhydride having the formula

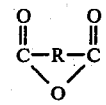

wherein R is a divalent hydrocarbon having 2 to 6 carbon atoms selected from the group consisting of alkylene, alkenylene, cyclohexylene, phenylene and tetrahydrophenylene, reacting 1 mol of the tricyclo[5.2.1.0.$^{2.6}$]-decane derivatives obtained, having the formula

wherein B represents the radical

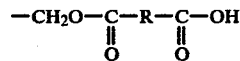

wherein R has the above-assigned values, with 2 mols of glycidyl (meth)acrylate, having the formula

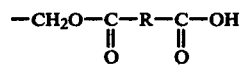

wherein $R_1$ is a member selected from the group consisting of hydrogen and methyl, and recovering said (meth)acrylic acid ester of tricyclo[5.2.1.0.$^{2.6}$]-decane derivatives.

In order to produce the half-esters, the isomeric or individual di-(hydroxymethyl)-tricyclo[5.2.1.0.$^{2.6}$]-decanes are reacted with dicarboxylic acid anhydrides such as maleic acid anhydride, succinic acid anhydride, phthalic acid anhydride, cyclohexane-dicarboxylic acid anhydride and tetrahydrophthalic acid anhydride in the ratio 1:2. The reaction is conducted, solvent-free, at a temperature of from 80° C. to 120° C. under a protective gas atmosphere if necessary, or optionally in the presence of an inert solvent. In order to accelerate the esterification reaction, suitable catalysts, such as quaternary ammonium compounds, may be added. The compounds thus obtained, tricyclo[5.2.1.0.$^{2.6}$]-decane derivatives having the formula

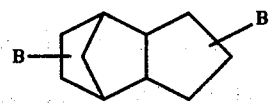

wherein B represents the radical

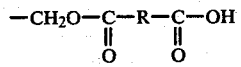

wherein R is a divalent hydrocarbon having 2 to 6 carbon atoms, selected from the group consisting of alkylene, alkenylene, cyclohexylene, phenylene and tetrahydrophenylene, are highly viscous substances which, however, are produced in a crystalline form, or can be crystallized, according to the choice of the acid component.

Further reaction to form compounds in accordance with the formula

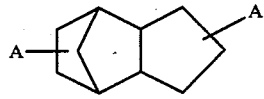

wherein A=

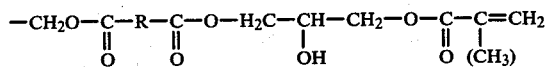

and R has the above-assigned values, and more particularly

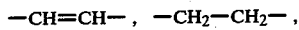

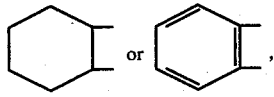

is effected by reacting the bis half-esters of the isomeric or individual di-(hydroxymethyl)-tricyclo-decanes with glycidyl (meth)acrylate in the molar ratio 1:2, that is, 1 mol of glycidyl (meth)acrylate is used for each 1 mol of carboxyl group. This reaction is effected, solvent-free, at temperatures of from 60° C. to 100° C. in the presence of atmospheric oxygen. The period of reaction lies between 1 to 8 hours.

The reaction products are raw materials for polymerizable adhesive systems. Advantageously, products of reaction, free from epoxide groups, of glycidyl (meth)acrylate and bis half-esters of di-(hydroxymethyl)-tricyclo[5.2.1.0.$^{2,6}$]-decanes are present in such systems in quantities of up to 90%.

The invention therefore also relates to an anaerobically setting adhesive and sealing composition comprising methacrylic or acrylic acid esters and organic hydroperoxides, which contains from 10% to 90% by weight based on the total weight of the polymerizable portion of the composition of the above product of reaction, free from epoxide groups, of glycidyl (meth)acrylate and bis half-esters of di-(hydroxymethyl)-tricyclo[5.2.1.0.$^{2,6}$]-decanes.

In addition to the products of the invention, up to 50% by weight, based on the total weight of the polymerizable portion, of further polymerizable components may be present. The further polymerizable components are cycloaliphatic, heterocyclic, or aliphatic (meth)acrylic acid esters. These cycloaliphatic, heterocyclic or aliphatic (meth)acrylic acid esters can contain free OH-groups. Particularly suitable esters containing free OH-groups are the monoesters of polyvalent alcohols having 2 to 6 carbon atoms, such as the hydroxyalkylmethacrylates, e.g., hydroxyethyl- and 2-hydroxypropyl-methacrylate.

These cycloaliphatic, heterocyclic, or aliphatic (meth)acrylic esters as components of anaerobic systems have been known for a long time. They are composed, for example, of (meth)crylic esters of mono- or polyvalent alcohols, such as ethylene glycol; diethylene glycol; tri-ethylene glycol; tetraethylene glycol; polyethylene glycol; glycerin; tri-methylol propane; pentanediol; di-, tri-, or tetrapropylene glycol; or the (meth)-acrylic esters of dimerized or polymerized cyclopentadienol; tetrahydrofurfuryl alcohol, cyclopentanol, methylcyclopentanol, cyclohexanol, methylcyclohexanol, 1,3-dioxa-2,2-dimethyl-4-methylol-cyclopentane or 4-methylolcyclohexane. The reaction products of glycide ethers of polyvalent phenols with acrylic acid or (meth)acrylic acid provide another group of anaerobically hardening adhesives. Those (meth)acrylic esters containing free OH-groups have been found to be very useful, as e.g., hydroxyethyl methacrylate, and 2-hydroxypropyl methacrylate. Satisfactory results are also obtained with esters produced by reacting (meth)acrylic acid with dimerized cyclopentadiene, i.e., (meth)-acrylic acid esters of the isomeric di-hydrodicyclopentadienols.

Among the cycloaliphatic, heterocyclic or aliphatic (meth)acrylic esters, particularly suitable are monomethacrylates such as tetrahydrofurfuryl methacrylate, 5,6-dihydrocyclopentadienyl methacrylate, cyclohexylmethacrylate, ethylhexyl methacrylate, hydroxyethyl methacrylate, hydroxypropyl methacrylate; the methacrylic acid esters of glycerin or trimethylol propane; and dimethacrylates, such as ethylene glycol dimethacrylate, triethyleneglycol dimethacrylate and polyethylene glycol dimethacrylate.

In a preferred embodiment, the anaerobic compositions of the invention consist of mixtures of 70% to 80% by weight of the polymerizable components, of the products of reaction, free from epoxide groups, of glycidyl methacrylate and the bis half-esters of di-(hydroxymethyl)-tricyclo-decanes, and 20% to 30% of mono(-meth)acrylates.

Another essential component of the anaerobically hardening compositions are the peroxide initiators. These are preferably hydroperoxides which derive from hydrocarbons with a chain length of 3 to 18 carbon atoms. Suitable, for example, are cumene hydroperoxide, tert.-butyl hydroperoxide, methyl ethyl ketone hydroperoxide, and diisopropyl benzene hydroperoxide, especially cumene hydroperoxide. Furthermore those peroxides are also suitable which have a half life period of 10 hours at a temperature between about 80° and 140° C. Here we mention particularly tert.-butyl perbenzoate, di-tert.-butyl-diperoxyphthalate, 2,5-dimethyl-2,5-bis-(tert.-butylperoxy)-hexane, bis-(1-hydroxy-cyclohexyl)peroxide, tert.-butyl-peroxyacetate, 2,5-dimethyl-hexyl-2,5-di-(peroxybenzoate), tert.-butylperoxy-isopropyl carbonate, n-butyl-4,4-bis-(tert.-butylperoxy) valerate, 2,2-bis-(tert.-butylperoxy)-butane and di-tert.-butyl peroxide.

The peroxides should be present in an amount of 0.1% to 20%, preferably 1.0% to 10%, based on the total weight of the polymerizable portions of the compositions. They are used mostly as phlegmatized (i.e., thickened) solutions or pastes, that is, with a relatively low content of inert substances, for example, dimethyl phthalate, cumene or the like.

The adhesives may also contain small amounts of auxiliary compounds such as are customarily present in adhesives of this type, such as stabilizers and, if desired, accelerators.

According to a preferred embodiment of the invention, stabilizers are added to the anaerobically hardening mixtures, particularly if they contain arylalkyl- and/or dialkyl hydrazones. The stabilizers prevent premature polymerization; that is, they improve the stability of the compositions during storage. Beyond that, they have an accelerating effect on the polymerization of the (meth)acrylic esters under anaerobic conditions. The stabilizers thus possess a double function. Suitable substances which have these properties are, for example, aliphatic monopercarboxylic acids, preferably the alkyl monopercarboxylic acids with 2 to 8 carbon atoms in the alkyl radical, (particularly peracetic acid) and nitrones, like C-phenyl-N-methyl-nitrone. Aromatic per acids can also be used, such as perbenzoic acid and perphthalic acid. The use of small amounts (e.g., 0.05% to 5.0%, preferably 0.05% to 3%, by weight of the (meth)acrylic esters) is generally sufficient.

In addition to the foregoing, the composition may contain a free radical stabilizer, to prevent gelations when oxygen alone is insufficient for the purpose. Quinones (for example, hydroquinone) are preferred stabilizers for this purpose. These quinone inhibitors can be used in concentrations of 100 to 1000 ppm, preferably 200 to 500 ppm, of the polymerizable portions of the compositions.

As a rule, the stabilizers are added as the last ingredient to the composition.

According to a preferred embodiment of the invention accelerators are added to the compositions. Suitable accelerators are the so-called imide accelerators such as benzoic acid sulfimide; particularly however, sulfohydrazide accelerators such as p-toluenesulfonic acid hydrazide, combined with a tert.-amine, preferably N,N-dimethyl-p-toluidine, and peracetic acid, are suitable as stabilizers. In order to obtain optimum properties of the adhesives or sealing agents, the accelerator and stabilizer must be added in ratios adjusted to one another. In general, they are used in quantities of from 0.1% to 3% by weight relative to the polymerizable components.

The components of the adhesive compositions of the present invention, including initiators, inhibitors, stabilizers, accelerators and esters, are mutually soluble or homogeneously dispersible.

An example of a preferred embodiment of the anaerobically hardening compositions of the invention consists of the (meth)acrylic acid esters of tricyclo [5.2.1.0.$^{2.6}$]-decane derivatives of the invention, mono(meth)acrylate(s), which can be substituted by free hydroxy group(s); a polymerizable carboxylic acid; an organic peroxide; an accelerator; and a stabilizer.

Furthermore, thickeners, softeners, plasticizers, inorganic fillers and coloring matter can also be added to the adhesive and sealing compounds according to the invention. Suitable thickening agents are polymeric compounds based on styrene or (meth)acrylic polymers, such as the ester-soluble poly (lower alkyl) acrylates and methacrylates, as e.g., polymethyl methacrylate and polyethyl acrylate, and ester-soluble polyvinyl hydrocarbons such as polystyrene, as well as polyvinyl chloride, synthetic rubber and the like. They are generally used in amount sufficient to give the composition a paste-like viscosity.

Among the fillers and colorants may be mentioned, e.g., finely-divided silicon dioxide, silicates, such as calcium silicate, bentonites, calcium carbonate, and titanium dioxide; and soluble dyes in amounts appropriate for the purpose.

The adhesive and sealing compositions according to the invention are produced by mixing the components at room temperature. These compositions have excellent storage stability in air or oxygen. They are stable for months or years if they are kept in vessels that are permeable to air, like polyethylene bottles. They can further be stored in only partly-filled bottles of glass, polyethylene, etc., without undergoing any change, a relatively low oxygen-partial pressure sufficing to inhibit polymerization. The bottles can also be colored to keep out short-wave light, which has a favorable effect on the stability.

The anaerobically hardening compositions of the present invention are used in the industry for cementing metal sheets or metal parts of different materials, as e.g., for the cementing of screws and bolts in their threads, the sealing of screw-connections, nipples, etc., the cementing of plug connections, the sealing of flanges, the assembly of intricate metal shapes, sealing pipe joints, etc. Assemblies of metals such as iron, brass, copper and aluminum can be bonded to each other. Small quantities of the adhesive compositions are introduced between the surfaces to be bonded, after which the surfaces are contacted with each other sufficiently firmly or in another manner so as to exclude air or oxygen. Then the compositions of the invention polymerize rapidly forming a firm bond. It is naturally also possible to accelerate the hardening with known means, as e.g., by heating the joint.

When the adhesives of the present invention are to be used for adhering or sealing glass or plastics or metals which are less catalytically active (for example, zinc, cadmium, high-alloyed steels and anodized aluminum), it is advantageous to pretreat these materials with metallic salt accelerators (for example, cooper naphthenate and cobalt naphthenate).

Among the advantages of the adhesive and sealing compositions according to the present invention are the following. Elevated temperatures are not required for hardening. The parts joined together can after a short time already be subject to heavy loading. In addition to ferrous materials, aluminum parts can also be cemented together with good strength. The thermal stability and flexibility of the cemented joint are excellent.

The adhesive obtainable in accordance with the invention is particularly suitable for bonding metals when great strength and satisfactory thermal stability of the glued joint are required. Thus, the adhesives in accordance with the invention are used in technology for the purpose of glueing plates or metal members made from various materials, for the purpose of securing bearing shafts, for sealing the joints in pipes and the like. A particularly striking feature is the relatively slight drop in the strength at 100° C. to 150° C. Almost 50% of the torque measured at room temperature can be observed even at 200° C.

The adhesives produced in accordance with the following samples and hardening under the exclusion of oxygen, were subjected to the following tests:

TESTING METHODS

(A) STABILITY TEST

In the stability test, test tubes of 10 cm in length and 10 mm in width were filled to 9/10ths of their capacity with the mixture according to Examples 1 to 6 and were suspended in a bath maintained at 80° C. The time which elapsed until the first gel formation was measured. All the samples were still free from gel after 60 minutes.

(B) TENSILE SHEARING STRENGTH

The tensile shearing strength according to DIN 53283 was measured on sand-blasted, singly overlapped test bodies made from steel plate (DIN 1541/ST 1203, 100×20×1.5 mm) and aluminum sheets (DIN 1783-AlCuMg 2 pl. 100×25×1.5 mm) (length of overlap 10 mm) on a tensile-testing machine (advance 20 mm/min) after hardening for 72 hours at room temperature.

(C) THERMAL STABILITY

The thermal stability was ascertained by means of the torque required to free glued nuts and bolts at various temperature. Bolts (N 10×30 DIN 933-8.8) and nuts (N 10 DIN 934-5.6) were glued and, after hardening for three days at room temperature, were stored for three days in a drying chamber at 150° C. and were subsequently clamped in a vice and the torque required to free the adhesive joint was determined by means of a torque wrench.

(D) COMPRESSIVE SHEARING STRENGTH

The compressive shearing strength was determined on glued sleeves made from steel ST 50 K (height 10 mm, diameter 20 mm) and bolts made from steel ST 50 K (height 10 mm, diameter 19.85 mm) after storing for three days at room temperature.

All the tests were made 5 times and the average value of the test results was then determined.

EXAMPLE 1

196 gm (1 mol) of di-(hydroxymethyl)-tricyclo [5.2.1.0.$^{2.6}$]-decane (isomeric mixture) and 196 gm (2 mols) of maleic acid anhydride were reacted at 100° C. under nitrogen in a non-metallic reaction vessel. The acid number was 289 (calculated 286) after a reaction period of 4 hours.

| Empirical formula C$_{20}$H$_{24}$O$_8$ | | (molecular weight 392.41) | |
|---|---|---|---|
| Calculated | C 61.2% | Calculated | H 6.16% |
| Found | C 61.4% | Found | H 6.24% |

The highly viscous bismaleic acid half-ester of di-(hydroxymethyl)-tricyclo [5.2.1.0.$^{2.6}$]-decane was reacted with 284 gm (2 mols) of glycidyl methacrylate at 80° C. in the presence of 300 ppm of hydroquinone. Air was conducted through the preparation during the reaction. The acid number was 8 after a reaction period of 10 hours, and the epoxide content was less than 1%. In the IR spectrum, the carboxy absorption band had disappeared at 3,050 cm$^{-1}$, and the band characteristic of hydroxyl groups, appeared at 3,500 cm$^{-1}$. The yield was 675 gm. The dimethacrylic acid ester was highly viscous at room temperature.

Refractive index: $n_D^{30} = 1,5126$.

| Empirical formula C$_{34}$H$_{44}$O$_{14}$ | | (molecular weight 676.72) | |
|---|---|---|---|
| Calculated | C 60.4% | Calculated | H 6.55% |
| Found | C 60.5% | Found | H 6.39% |

EXAMPLE 2

196 gm (1 mol) of di-(hydroxymethyl)-tricyclo[5.2.1.0.$^{2.6}$]-decane (isomeric mixture), 130 gm (1.33 mols) of maleic acid anhydride and 99 gm (0.67 mols) of phthalic acid anhydride were reacted at 100° C. under nitrogen in a non-metallic reaction vessel. The acid number was 267 (calculated 264) after a reaction period of four hours.

| (molecular weight = 425) | | |
|---|---|---|
| Calculated | C 63.9% | H 6.00% |
| Found | C 64.0% | H 6.01% |

The highly viscous, mixed bis half-ester of di-(hydroxymethyl)-tricyclo[5.2.1.0.$^{2.6}$]-decane was reacted with 284 gm (2 mols) of glycidyl methacrylate at 80° C. with the feeding of air therethrough in the presence of 300 ppm hydroquinone. The acid number was 10 after 10 hours, and the residual expoxy content was less than 1%. The yield was 705 gm. The dimethacrylic acid ester was highly viscous at room temperature.

Refractive index: $n_D^{30} = 1,5226$.

| (molecular weight = 709) | | |
|---|---|---|
| Calculated | C 62.0% | H 6.43% |
| Found | C 62.2% | H 6.43%. |

EXAMPLE 3

98 gm (0.5 mol) of di-(hydroxymethyl)-tricyclo[5.2.1.0.$^{2.6}$]-decane (isomeric mixture) and 148 gm (1 mol) of phthalic acid anhydride were reacted at 100° C. under nitrogen in a non-metallic reaction vessel. The acid number was 229 (calculated 228) after a reaction period of four hours.

| Empirical formula C$_{28}$H$_{28}$O$_8$ | | (moleculr weight = 492.53) | |
|---|---|---|---|
| Calculated | C 68.2% | H 5.83% | m.p. 71°–73° C. |
| Found | C 67.9% | H 5.48% | |

The bisphthalic acid half-ester of di-(hydroxymethyl)-tricyclo[5.2.1.0.$^{2.6}$]-decane was reacted with 142 gm (1 mol) of glycidyl methacrylate at 80° C. with the feeding of air therethrough in the presence of 300 ppm hydroquinone. The acid number was 9 after 15 hours. The yield was 380 gm. The dimethacrylic acid ester was highly viscous at room temperature.

| Empirical formula C$_{42}$H$_{48}$O$_{14}$. | | (molecular weight = 776.84) |
|---|---|---|
| Calculated | C 64.9% | H 6.23% |
| Found | C 64.9% | H 6.44% |

Refractive index: $n_D^{30} = 1,5410$.

EXAMPLE 4

The following adhesive mixture was prepared with the compound of Example 1:

75 gm of dimethacrylic acid ester (Example 1)
18 gm of hydroxyethyl methacrylate
0.25 gm of p-toluene sulfonic acid hydrazide
0.5 gm of N,N-dimethyl-p-toluidine
5 gm of a 70% solution of cumene hydroperoxide in cumene 1.25 gm of a 40% solution of peracetic acid in acetic acid Glued joints were made with this liquid adhesive and the following average values were found after hardening at room temperature:
Tensile shearing strength on steel—312 kp/cm²
Tensile shearing strength on aluminum—161 kp/cm²
Compressive shearing strength on steel—288 kp/cm²

The thermal stability was ascertained on nuts and bolts:
Torque at room temperature—650 kpcm
Torque at 100° C.—450 kpcm
Torque at 150° C.—350 kpcm
Torque at 200° C.—300 kpcm

EXAMPLE 5

The following adhesive mixture was prepared with the reaction product of Example 2:
75 gm of dimethacrylic acid ester (Example 2)
18 gm of hydroxyethyl methacrylate
0.5 gm of p-toluene sulfonic acid hydrazide
0.5 gm of N,N-dimethyl-p-toluidine
5 gm of a 70% solution of cumene hydroperoxide in cumene
1 gm of a 40% solution of peracetic acid in acetic acid Glued joints were made with this liquid adhesive, and the following average values were found after hardening at room temperature:
Tensile shearing strength on steel—338 kp/cm²
Tensile shearing strength on aluminum—145 kp/cm²
Compressive shearing strength on steel—352 kp/cm²

The thermal stability was ascertained on nuts and bolts:
Torque at room temperature—600 kpcm
Torque at 100° C.—450 kpcm
Torque at 150° C.—350 kpcm
Torque at 200° C.—240 kpcm

EXAMPLE 6

The following adhesive mixture was prepared with the reaction product of Example 3:
75 gm of dimethacrylic acid ester (Example 3)
18 gm of hydroxyethyl methacrylate
0.5 gm of p-toluene sulfonic acid hydrazide
0.5 gm of N,N-dimethyl-p-toluidine
5 gm of a 70% solution of cumene hydroperoxide in cumene
1 gm of a 40% solution of peracetic acid in acetic acid Glued joints were made with this liquid adhesive, and the following average values were found after hardening at room temperature:
Tensile shearing strength on steel—350 kp/cm²
Tensile shearing strength on aluminum—132 kp/cm²
Compressive shearing strength on steel—370 kp/cm²

The thermal stability was ascertained on nuts and bolts:
Torque at room temperature—600 kpcm
Torque at 100° C.—450 kpcm
Torque at 150° C.—300 kpcm
Torque at 200° C.—180 kpcm The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. (Meth)acrylic acid esters of tricyclo[5.2.1.0.$^{2,6}$]-decane derivatives having the formula

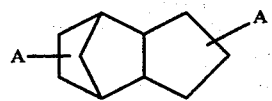

wherein A represents substituents in the positions selected from the group consisting of 3,8-, 3,9-, 4,8- and isomeric mixtures thereof, said substituents being the radical

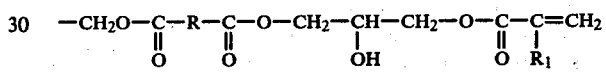

wherein R is a divalent hydrocarbon having 2 to 6 carbon atoms derived from a dicarboxylic acid which forms internal anhydrides selected from the group consisting of alkylene, alkenylene, cyclohexylene, phenylene, tetrahydrophenylene, and mixtures thereof, and $R_1$ is a member selected from the group consisting of hydrogen and methyl.

2. The (meth)acrylic acid esters of claim 1 wherein $R_1$ is methyl.

3. The (meth)acrylic acid esters of claim 2 wherein the A substituents are isomeric mixtures and R is ethenylene.

4. The (meth)acrylic acid esters of claim 2 wherein the A substituents are isomeric mixtures and R is phenylene.

5. The (meth)acrylic acid esters of claim 2 wherein the A substituents are isomeric mixtures and R is a mixture of ethenylene and phenylene.

* * * * *